United States Patent [19]
Imaizumi et al.

[11] Patent Number: 5,991,018
[45] Date of Patent: Nov. 23, 1999

[54] APPARATUS AND METHOD FOR INSPECTING COATING LAYER

[75] Inventors: Junjirou Imaizumi; Tsutomu Amano; Yoshimoto Take, all of Tokyo; Yoshito Amino, Shinnanyou, all of Japan

[73] Assignee: Kirin Beer Kabushiki Kaisha, Tokyo, Japan

[21] Appl. No.: 08/973,459

[22] PCT Filed: Jun. 12, 1996

[86] PCT No.: PCT/JP96/01586

§ 371 Date: Dec. 15, 1997

§ 102(e) Date: Dec. 15, 1997

[87] PCT Pub. No.: WO96/41643

PCT Pub. Date: Dec. 27, 1996

[30] Foreign Application Priority Data

Jun. 14, 1995 [JP] Japan .................................. 7-147752
Aug. 11, 1995 [JP] Japan .................................. 7-206013

[51] Int. Cl.⁶ .................................................. G01N 21/00
[52] U.S. Cl. ...................................... 356/239.1; 356/237.1; 356/239.4
[58] Field of Search ..................................... 356/240, 378, 356/428, 448, 394, 201; 209/587, 911, 657, 606, 642, 655, 576, 552, 522–524, 111.7; 250/223, 562, 572, 556, 338, 341

[56] References Cited

U.S. PATENT DOCUMENTS

| | | | |
|---|---|---|---|
| 3,749,923 | 7/1973 | Husome | 250/223 |
| 4,017,194 | 4/1977 | Conroy et al. | 356/240 |
| 4,693,376 | 9/1987 | Marion et al. | 209/552 |
| 4,791,287 | 12/1988 | Fisher | 356/240 |
| 4,859,863 | 8/1989 | Schrader et al. | 250/556 |
| 5,139,406 | 8/1992 | Hoshino et al. | 425/140 |
| 5,755,335 | 5/1998 | Michelotti et al. | 209/528 |

FOREIGN PATENT DOCUMENTS

| | | |
|---|---|---|
| 0 429 086 | 5/1991 | European Pat. Off. . |
| 0 485 646 | 5/1992 | European Pat. Off. . |
| 58-178206 | 10/1983 | Japan . |
| 58-184537 | 10/1983 | Japan . |
| 62-135707 | 6/1987 | Japan . |

*Primary Examiner*—Frank G. Font
*Assistant Examiner*—Michael P. Stafira
*Attorney, Agent, or Firm*—Oblon, Spivak, McClelland, Maier & Neustadt, P.C.

[57] ABSTRACT

An apparatus for inspecting a thickness or deteriorating situation of a coating layer formed on a surface of a container, which includes an inspecting light irradiating unit to irradiate an inspecting light to a container with a coating layer formed thereon, an image pickup unit to receive a reflected light or a transmission light of the inspecting light irradiated by the inspecting light irradiating unit and reflected from the container or passing through the container, and to convert the reflected light or the transmission light into an image pickup signal and to output same, and an determining unit to determine a thickness or a deteriorating situation of the coating layer formed on the container by inputting the image pickup signal outputted from the image pickup unit and comparing an image pickup data indicated by the image pickup signal with a prememorized standard data.

20 Claims, 11 Drawing Sheets

| C.I.E value/coating thickness (A) | 0 | 450 | 810 | 1300 |
|---|---|---|---|---|
| X | 0.300 | 0.322 | 0.350 | 0.392 |
| Y | 0.254 | 0.277 | 0.320 | 0.371 |

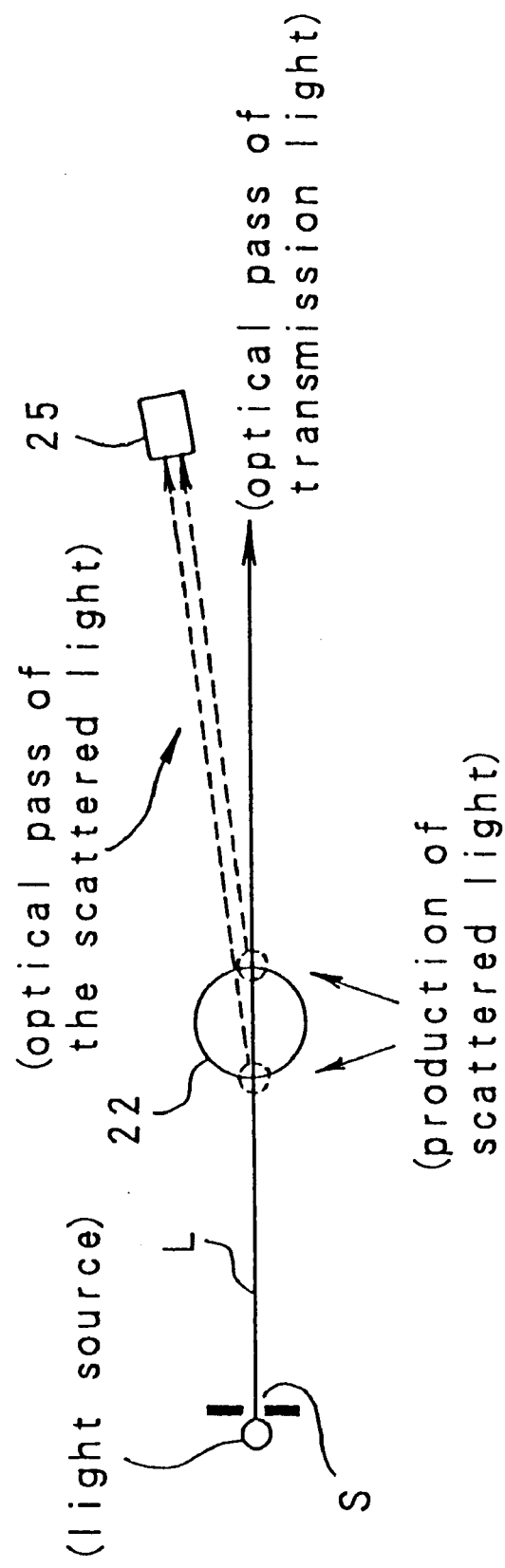

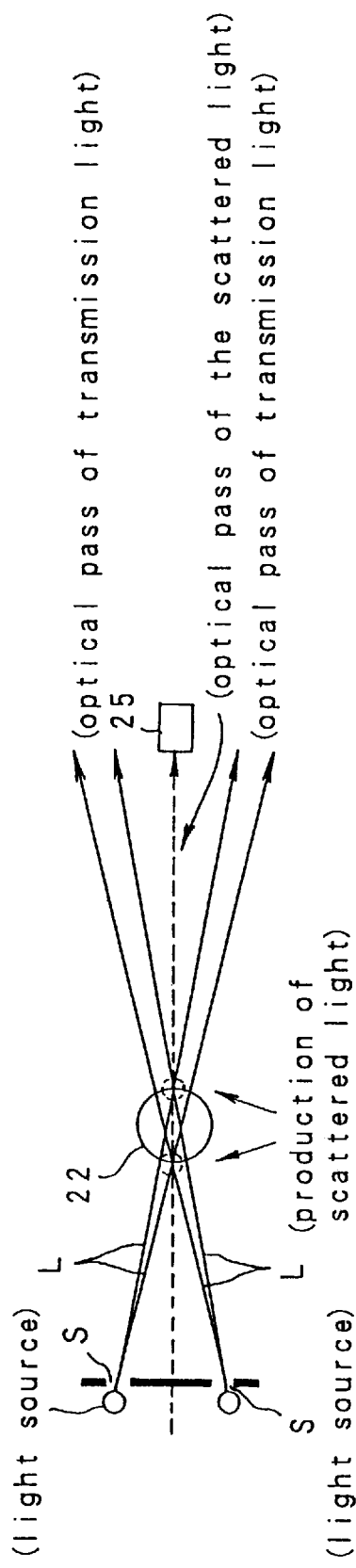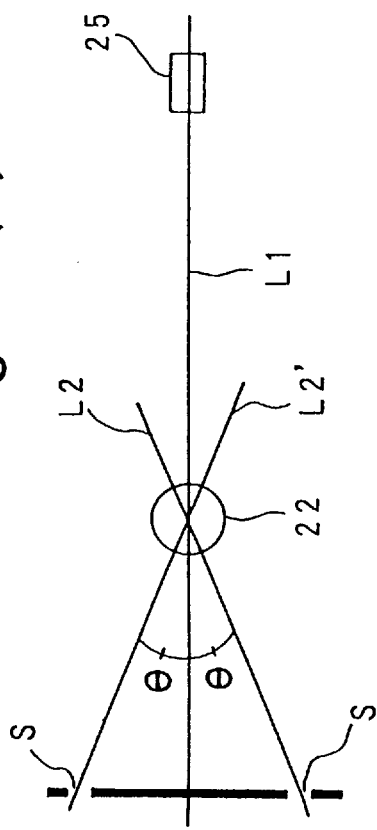

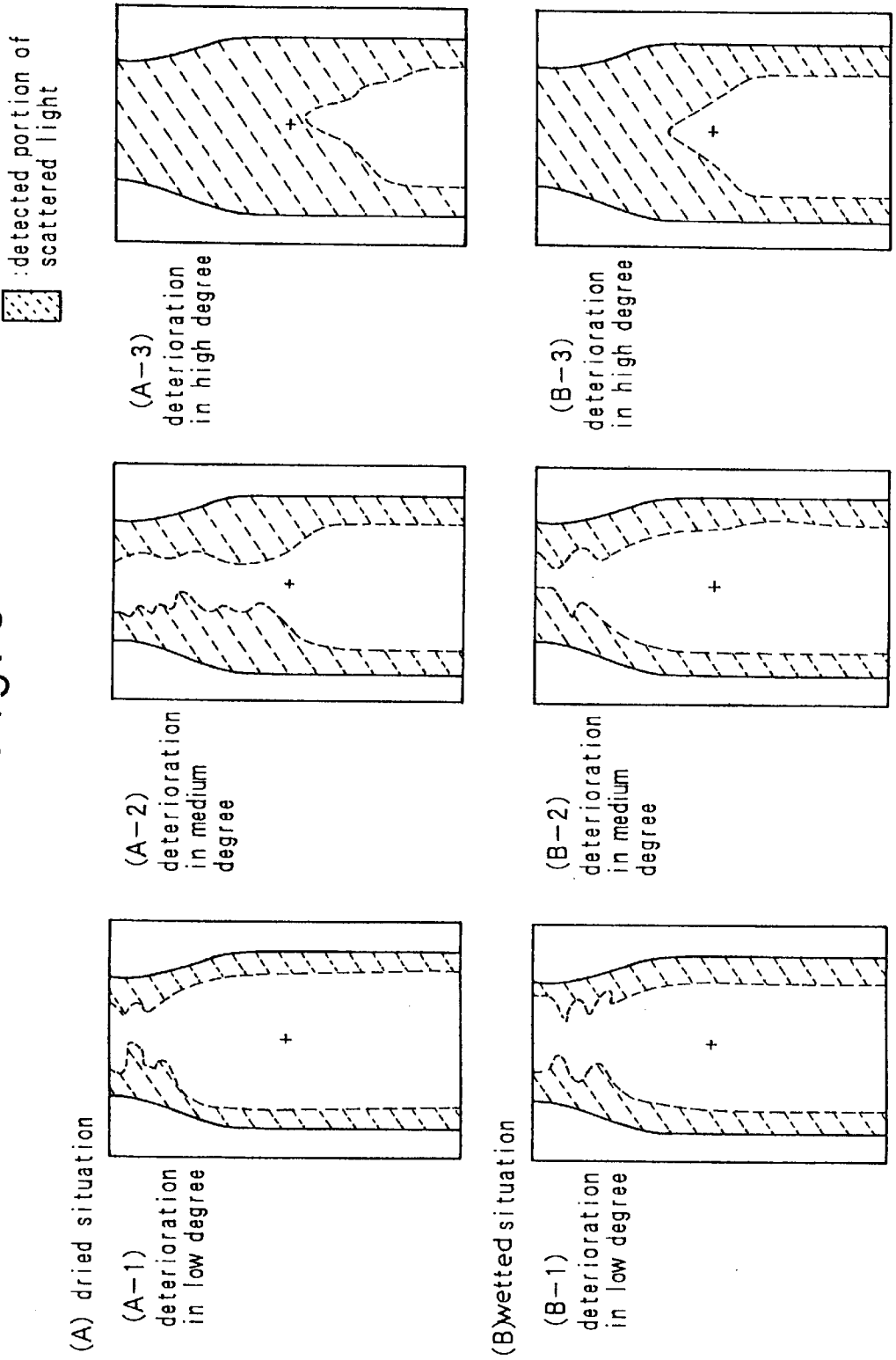

- fluorescent lamp scattering illumination
- slit interval 50mm
- slit width 8mm

| grade | 0 | 1 | 2 | 3 | 4 | 5 |
|---|---|---|---|---|---|---|
| dried situation (mean) A | 55.1 | 71.5 | 77.1 | 82.5 | 94.6 | 98.6 |
| wetted situation (mean) B | 53.2 | 58.1 | 62.7 | 68.8 | 82.6 | 87.2 |
| A−B | 1.9 | 13.4 | 14.4 | 13.7 | 12 | 11.4 |

APPARATUS AND METHOD FOR INSPECTING COATING LAYER

FIELD OF THE INVENTION

The present invention relates to apparatus and methods for inspecting conditions of a coating layer applied on a surface of a container such as a bottle, more specifically relates to apparatus and methods for inspecting thickness and deteriorating situation of a coating layer applied on a surface of a container so as to maintain sufficient strength of the container which is lightened in weight.

BACKGROUND OF THE INVENTION

As a container used for filling beverages, for example, a container such as a bottle made of glass has been widely used.

Recently, the bottle mentioned above is to be lightened in weight in order to benefit convenience in transportation thereof. A means of forming a coating layer on the surface of the bottle is applied in order to prevent the bottle from weakening in strength due to the introduction of lightening the bottle in weight. Metal oxide coating layer such as SnO2 or TiO2 is formed by means of a so-called hot end coating process on the surface of the bottle for this purpose.

The hot end coating process is a technique in which a reaction gas is sprayed on the surface of the bottle, during the time when the surface thereof still has a relatively higher temperature prior to the application of a slow cooling thereto upon manufacturing the bottle, to form an oxide coating layer of SnO2 or TiO2 on the surface of the bottle.

The thickness of the coating layer should fall within a prescribed scope to maintain a mechanical strength (i.e., durability) of the bottle. With a thin coating layer outside the scope, bottles contact with each other upon transporting thereof to result in causing a scratch on the surface of the bottle so that it becomes difficult to maintain the desired strength of the bottle, thus cracking the bottle.

On the other hand, with a thick coating layer outside the scope, a rainbow-like pattern is produced on the surface of the bottle due to the interference of the light (especially, in a visible light range), which pattern looks like a oil film adhering on the surface of the bottle, to result in deteriorating a fine view, lowering the value of the commodity and wasting the reaction gas.

Accordingly, it is desirable to severely inspect the thickness of the coating layer formed on the surface of the bottle.

Conventionally, the inspection of the thickness of the coating layer formed on the surface of the bottle has been carried out by an apparatus for measuring the thickness thereof by means of contacting the bottle to be inspected (hereinafter referred to as a "contact-type measuring apparatus"), for example, a hot end coating meter manufactured by American Glass Research, Inc. Thereby the thickness of the coating layer is detected and measured by contacting a light emitting/sensoring device with the surface of the bottle.

However, in the contact-type measuring apparatus, it is necessary to adjust an angle of the light emitting/sensoring device so as to receive the maximum amount of the light. There is therefore a problem that it requires a well trained skill to measure the thickness of the coating layer, and furthermore, even a man of well trained skill has to take time to do the same.

Furthermore, in the contact-type measuring apparatus, silicone oil as an optical coupling fluid has to be immersed on the surface of the bottle when the light emitting/sensoring device is contacted with the bottle. It is therefore necessary to wipe out the immersion fluid after the thickness is measured. Because it takes time to wipe out the painted oil, the bottles used for measuring the thickness of the coating layer are discarded in general.

In general, the bottles are sampled to detect and measure the thickness of the coating layer in the manufacturing process of the bottles. It is therefore necessary to increase the number of the inspections in order to obtain the overall information about the situation of the coating layer of the manufactured bottles, thus increasing the number of bottles to be discarded, and lowering efficiency of the inspection.

Japanese Patent Provisional Publication No. 131,547/91 discloses a bottle to be recycled and repeatedly used with a coating layer formed on the surface thereof (which has a SnO2 coating layer of about 100 nm thickness)(hereinafter referred to as a "returnable bottle") so as to lighten the weight of the bottle for beverages like beer and increase the number of repetitive use.

However, the above-mentioned conventional contact-type measuring apparatus has a problem that it can measure only the thickness of the coating layer up to about 60 nm, it is impossible to detect and measure the thickness of the coating layer of about 100 nm mentioned above.

In addition, a bottle with a prescribed thickness of a coating layer formed on the surface thereof can be recycled and used, thus increasing the number of the repetitive use of the bottle. However, since the returnable bottle collected from the market is in general repetitively washed in a washing machine with the use of a heated alkaline solution (for example, 4% of a caustic soda aqueous solution at the temperature of 80° C.), the coating layer on the surface of the bottle may be deteriorated by the heated alkaline solution.

Due to the deterioration of the coating layer, the surface of the bottle looks like a whitish, thus deteriorating a fine external view of the bottle to lower the value of the commodity as a bottled product, even if the bottle has a sufficient strength to be recycled and used.

More specifically, the coating layer, for example, the SnO2 coating layer has pinholes from 2 to 3 $\mu$m in diameter therein from the beginning, as illustrated in FIG. 13(a). Then, the coating layer is repeatedly washed in the heated alkaline solution so that the pinholes gradually grow deeper and larger up to about 10 $\mu$m in diameter, as illustrated in FIG. 13(b).

When the pinholes grow so large as mentioned above, a light passing through the bottle is scattered by the pinholes in the coating layer. Furthermore, when the number of the pinholes increase, the color of the coating layer turns gradually from an original pale gold to silver, thus lowering its transparency.

When the number of the pinholes increase more, the surface of the bottle becomes like a ground glass so that the overall or part of the surface of the bottle lose a shine, resulting in looking like a whitish. The bottles with remarkably deteriorated coating layer on the surface thereof have to be discarded even if they have a sufficient strength to be recycled.

The separation of the bottles with a deteriorated coating layer from those with a good coating layer has been carried out by an inspector by means of the observation with his eyes.

However, there is a problem in the detection of the deteriorated coating layer by means of the observation with the eyes that it is difficult to establish an objective index to identify the extent of the deterioration. Thus, the accuracy of the inspection has to be left to the subjective judgement of the respective inspectors themselves to cause a different result in the respective judgements. In addition, there is a problem that the observation with the eyes by the inspector inclines to causing an oversight or limits the inspecting speed.

The present invention is made to solve the above mentioned problems in the inspection of the thickness or deteriorating situation of the coating layer formed on the surface of the bottle.

More specifically, the purpose of the present invention is to provide an apparatus and method for inspecting a coating layer, in which a thickness of the coating layer formed on the surface of the bottle can be measured without contacting the bottle, the inspection of the bottles can be carried out not to the selected sampling bottles but to all the bottles, and even a coating layer having a thick thickness can be measured.

Another purpose of the invention is to provide an apparatus and method for inspecting a coating layer, in which the deteriorating situation of the coating layer formed on the surface of the bottle can be automatically operated and differentiated on the basis of an objective standard, and a high inspecting speed is possible.

SUMMARY OF THE INVENTION

In order to attain the above-mentioned purposes, an apparatus for inspecting a coating layer of the first invention is an apparatus for inspecting a thickness or deteriorating situation of a coating layer formed on a surface of a container, which includes:

an inspecting light irradiating means to irradiate an inspecting light to a container with a coating layer formed thereon;

an image pickup means to receive a reflected light or a transmission light of the inspecting light irradiated by the inspecting light irradiating means and reflected from the container or passing through the container, and to convert the reflected light or the transmission light into an image pickup signal; and an operating means to operate a thickness or a deteriorating situation of the coating layer formed on the container by inputting the image pickup signal outputted from the image pickup means and comparing an image pickup data indicated by the image pickup signal with a prememorized standard data.

In the apparatus for inspecting a coating layer of the first invention, the inspecting light is irradiated from the inspecting light irradiating means to the container like a bottle made of a transparent material like glass and the like with a coating layer formed on the surface thereof. This inspecting light either is reflected from the surface of the container or passes through the container dependent on its irradiating angle. The image pickup means receives either the reflected light from the container of the inspecting light or the transmission light passing through the container to convert those reflected light or transmission light into the image pickup signal. At that time, when the inspecting light is reflected from the surface of the container, a spectral distribution of the reflected light varies depending on a thickness of the coating layer formed on the surface of the container. In addition, in case that so-called pinholes are produced in the coating layer due to a deterioration of the coating layer of the container, when the inspecting light transmits the container, the inspecting light transmitting the container is scattered. The amount of thus scattered light varies depending on the deteriorating situation of the coating layer and increases as the deterioration progresses. Since the image pickup signal outputted from the image pickup means includes data relating to the coating layer which is contained in those reflected light or scattered light, the operating means operates the thickness or the deteriorating situation of the coating layer formed on the container by comparing the image pickup data contained in the above-mentioned image pickup signal with the prememorized standard data relating to the spectral distribution or the amount of the scattered light.

As described above, according to the first invention, it is possible to automatically operate a situation of the coating layer formed on the surface without contacting the bottle to be inspected and on a basis of an objective standard.

In order to attain the above-mentioned purposes, an apparatus for inspecting a coating layer of the second invention is an apparatus according to the first invention, wherein:

the inspecting light irradiating means irradiates the inspecting light having a prescribed spectral distribution;

the image pickup means is placed at a location to receive the reflected light of the inspecting light from the container;

the standard data comprises a standard spectral distribution premeasured correspondingly to a thickness of a coating layer; and the operating means operates a thickness of the coating layer by comparing a spectral distribution received by the image pickup means with the standard spectral distribution.

In the apparatus for inspecting a coating layer of the second invention, the inspecting light irradiated from the inspecting light irradiating means has a specific spectral distribution, and the reflected light from the container is received by the image pickup means. When the inspecting light is reflected from the container, the spectral distribution of the inspecting light varies under the effect of the coating layer formed on the container. It varies largely as the thickness of the coating layer becomes thicker. The standard spectral distribution premeasured correspondingly to the thickness of the coating layer is memorized as the standard data in the operating means. The operating means operates the thickness of the coating layer of the container by comparing the data relating to the spectral distribution of the reflected light contained in the image pickup signal with the spectral distribution of the standard data.

As described above, according to the second invention, it is possible to measure the thickness of the coating layer formed on the surface without contacting the bottle to be inspected, thus, enabling to carry out the inspection not to containers chosen by sampling but to all the containers. In addition, it is possible even to measure the thickness of the thicker coating layer.

In order to attain the above-mentioned purposes, an apparatus for inspecting a coating layer of the third invention is an apparatus according to the second invention, wherein:

an irradiating angle of the inspecting light of the inspecting light irradiating means to the coating layer of the container is within a range of 30° to 60°.

In the apparatus for inspecting a coating layer of the third invention, because the irradiating angle of the inspecting light of the inspecting light irradiating means to the coating layer of the container is within the range of 30° to 60°, the variation of the spectral distribution in the reflected light from the container becomes remarkable, thus, enabling a correct measurement of the coating layer.

In order to attain the above-mentioned purposes, an apparatus for inspecting a coating layer of the fourth invention is an apparatus according to the second invention, wherein:

the inspecting light irradiating means comprises a surface illuminant and a color temperature of the irradiated inspecting light is fixed to be about constant.

In the apparatus for inspecting a coating layer of the forth invention, the inspecting light is irradiated from the inspecting light irradiating means comprising the surface illuminant to the container. Because of this features, the location of the container to be placed for the inspection is not strictly required, thus enabling a stable inspection. In addition, because the color temperature of the inspecting light is fixed to be about constant, a color temperature correction and the like of the inspecting light is not necessary, thus enabling a further stable inspection.

In order to attain the above-mentioned purposes, an apparatus for inspecting a coating layer of the fifth invention is an apparatus according to the second invention, wherein:

the apparatus further includes a location detecting means to detect for a transported container to be placed at a prescribed inspecting location, and to output a detecting signal; and the operating means operates a thickness of the coating layer by taking therein the image pickup signal outputted from the image pickup means upon inputting therein the detecting signal outputted from the location detecting means.

In the apparatus for inspecting a coating layer of the fifth invention, when the inspection of the coating layer of the container, which is sequentially transported by means of the transporting means like a conveyer, is continuously carried out by the inspection apparatus fixed to the transporting means, the location detecting means detects the fact that the transported container is placed at the specific location. Then, the operating means operates the thickness of the coating layer by taking in the image pickup signal outputted from the image pickup means upon inputting the detecting signal of the container outputted from the location detecting means. Because of this feature, it is possible to continuously measure the thickness of the coating layer of the container which is sequentially transported in the transporting line of the container, thus enabling the overall measurement of the thickness of the coating layer of all the containers.

In order to attain the above-mentioned purposes, an apparatus for inspecting a coating layer of the sixth invention is an apparatus according to the first invention, wherein:

the image pickup means is placed at a location to receive a scattered light produced upon a transmission of the inspecting light irradiated from the inspecting light irradiating means through the container;

the standard data comprises a data indicating a deteriorating situation of a coating layer prefixed correspondingly to a deteriorating situation of a coating layer; and the operating means operates the deteriorating situation of the coating layer of the container by comparing a data based on an amount of the scattered light received by the image pickup means with the standard data.

In the apparatus for inspecting a coating layer of the sixth invention, when the transmission light is caused to scatter at the time the inspecting light irradiated from the inspecting light irradiating means passes through the container, the scattered light is received by the image pickup means. The scattering of the inspecting light is caused to produce by the so-called pinholes formed in the coating layer when the coating layer of the container deteriorates, and the amount of the scattered light increases as the deterioration of the coating layer progresses. In the operating means, the amount of the scattered light, which indicates the deterioration situation of the coating layer preset correspondingly to the deterioration situation of the coating layer, is memorized as the standard data. The operating means operates the deteriorating situation of the coating layer of the container by comparing the data indicating the amount of the scattered light contained in the image pickup signal with the standard data.

As described above, according to the sixth invention, it is possible to automatically differentiate the deteriorating situation of the coating layer formed on the surface of the container and the like on a basis of an objective standard, and to carry out a speedy inspection.

In order to attain the above-mentioned purposes, an apparatus for inspecting a coating layer of the seventh invention is an apparatus according to the sixth invention, wherein:

the image pickup means is placed at a location to only receive the scattered light and not to receive the inspecting light passing through the container without producing the scattered light.

In the apparatus for inspecting a coating layer of the seventh invention, the image pickup means receive only the scattered light produced by the deteriorated coating layer out of the inspecting light passing through the container and does not receive the transmission light passing through without producing the scattering. As a result, it is possible to carry out a correct inspection without being affected by the light which does not indicate the deteriorating situation of the coating layer, and to easily identify a minimal difference of the deterioration of the coating layer.

In order to attain the above-mentioned purposes, an apparatus for inspecting a coating layer of the eighth invention is an apparatus according to the sixth invention, wherein:

the inspecting light irradiating means has a light source and a slit member having a slit placed between the light source and an inspecting location of the container, and producing a slit type inspecting light by passing a light irradiated from the light source through the slit.

In the apparatus for inspecting a coating layer of the eighth invention, the slit type inspecting light is produced by passing the light irradiated from the light source through the slit formed in the slit member, and is irradiated to the container. As a result, unnecessarily diffusion of the inspecting light is prevented by passing the light irradiated from the light source through the slit and then, irradiating to the container, and the affection of the inspecting light excluding the scattered light produced in accordance with the deterioration of the coating layer is reduced, thus enabling a further precise inspection.

In order to attain the above-mentioned purposes, an apparatus for inspecting a coating layer of the ninth invention is an apparatus according to the eighth invention, wherein:

the slit member has a plurality of slits.

In the apparatus for inspecting a coating layer of the ninth invention, since the slit member has a plurality of slits, a plurality of slit type inspecting lights are irradiated to one container. As a result, it is not necessary to strictly locate the container to be inspected at the inspecting location, thus enabling to carry out an easier and more reliable inspection.

In order to attain the above-mentioned purposes, an apparatus for inspecting a coating layer of the tenth invention is an apparatus according to the sixth invention, wherein:

the apparatus further includes a location detecting means to detect for a transported container to be placed at a prescribed inspecting location, and to output a detecting signal;

the operating means operates a deteriorating situation of the coating layer by taking therein the image pickup signal outputted from the image pickup means upon inputting therein the detecting signal outputted from the location detecting means.

In the apparatus for inspecting a coating layer of the tenth invention, when the inspecting apparatus is fixed to the transporting means like a conveyer or the like which transports the container to sequentially detect the coating layer of the transported container, it is detected that the transported container is placed at the specific inspecting location. Then, the operating means operates the deteriorating situation of the coating layer by taking in the image pickup signal outputted from the image pickup means when the detecting signal of the container outputted from the location detecting means. Thus, it is possible to automatically and sequentially inspect the coating layers of the containers which are continuously transported in the container transporting line.

In order to attain the above-mentioned purposes, a method for inspecting a coating layer of the eleventh invention is a method for inspecting a thickness or deteriorating situation of a coating layer formed on a surface of a container, which comprises:

an inspecting light irradiating step to irradiate an inspecting light to a container with a coating layer formed on a surface thereof;

an image pickup step to receive by an image pickup means a reflected light from the container of the inspecting light irradiated in the inspecting light irradiating step or a transmission light passing through the container, and to convert into an image pickup signal; and a operating step to operate a thickness or a deteriorating situation of the coating layer formed on the container by comparing an image pickup data of the image pickup signal of the reflected light or the transmission light converted in the image pickup step with a preset standard data.

In the method for inspecting a coating layer of the eleventh invention, the inspecting light, which is irradiated to the container like a bottle and the like made of the transparent material like glass with the coating layer formed on the surface thereof, either is reflected from the surface of the container or passes through the container depending on the irradiating angle thereof. When the inspecting light is reflected from the surface of the container, a spectral distribution of the reflected light varies depending on a thickness of the coating layer formed on the surface of the container. In addition, in case that the so-called pinholes are produced in the coating layer due to a deterioration of the coating layer of the container, when the inspecting light transmits the container, the inspecting light transmitting the container is scattered. The amount of thus scattered light varies depending on the deteriorating situation of the coating layer and increases as the deterioration progresses. Since the image pickup signal outputted from the image pickup means includes data relating to the coating layer which is contained in those reflected light or scattered light, the thickness or the deteriorating situation of the coating layer formed on the container is operated by comparing the image pickup data contained in the above-mentioned image pickup signal with the standard data relating to the spectral distribution or the amount of the scattered light.

As described above, according to the eleventh invention, it is possible to automatically operate a situation of the coating layer formed on the surface without contacting the bottle to be inspected and on a basis of an objective standard.

In order to attain the above-mentioned purposes, a method for inspecting a coating layer of the twelfth invention is a method according to the eleventh invention, which comprises:

in the inspecting light irradiating step, the inspecting light comprises a light having a prescribed spectral distribution;

in the image pickup step, the image pickup means is placed at a location to receive the reflected light from the container of the inspecting light; and in the operating step, the standard data comprises a standard spectral distribution premeasured correspondingly to a thickness of a said coating layer and a thickness of a coating layer is operated by comparing a spectral distribution of the reflected light indicated by the image pickup signal with the standard spectral distribution.

In the method for inspecting a coating layer of the twelfth invention, the inspecting light has the specific spectral distribution, and when the inspecting light is reflected from the container, the spectral distribution of the inspecting light varies under the effect of the coating layer formed on the container. It varies largely as the thickness of the coating layer becomes thicker. The image pickup signal outputted from the image pickup means contains the data relating to a variance of the spectral distribution of the reflected light. The thickness of the coating layer of the container is operated by comparing the data relating to the spectral distribution of the reflected light contained in the image pickup signal with the spectral distribution of the standard data.

As described above, according to the twelfth invention, it is possible to measure the thickness of the coating layer formed on the surface without contacting the container to be inspected, thus, enabling to carry out the inspection not to containers chosen by sampling but to all the containers. In addition, it is possible even to measure the thickness of the thicker coating layer.

In order to attain the above-mentioned purposes, a method for inspecting a coating layer of the thirteenth invention is a method according to the twelfth invention, which comprises:

in the inspecting light irradiating step, an irradiating angle of the inspecting light to the coating layer of the container is within a range of 30° to 60°.

In the method for inspecting a coating layer of the thirteenth invention, because the irradiating angle of the inspecting light of the inspecting light irradiating means to the coating layer of the container is within the range of 30° to 60°, the variation of the spectral distribution in the reflected light from the container becomes remarkable, thus, enabling a correct measurement of the coating layer.

In order to attain the above-mentioned purposes, a method for inspecting a coating layer of the fourteenth invention is a method according to the twelfth invention, which comprises:

in the inspecting light irradiating step, a light source comprises a surface illuminant, and a color temperature of the inspecting light irradiated from the surface illuminant is fixed to be about constant.

In the method for inspecting a coating layer of the fourteenth invention, the inspecting light is irradiated from the inspecting light irradiating means comprising the surface illuminant to the container. Because of this features, the location of the container to be placed for the inspection is not strictly required, thus enabling a stable inspection. In addition, because the color temperature of the inspecting light is fixed to be about constant, a color temperature correction and the like of the inspecting light is not necessary, thus enabling a further stable inspection.

In order to attain the above-mentioned purposes, a method for inspecting a coating layer of the fifteenth invention is a method according to the twelfth invention, which comprises:

in the operating step, a placement of a transported container at a prescribed inspecting location is detected and the thickness of the coating layer is operated on the basis of the image pickup signal outputted from the image pickup means upon detecting for the container to be placed at then prescribed location.

In the method for inspecting a coating layer of the fifteenth invention, when the inspection of the coating layer of the container, which is sequentially transported by means of the transporting means like a conveyer, is continuously carried out by the inspection apparatus fixed to the transporting means, it is detected that the transported container is placed at the specific location. Then, the thickness of the coating layer is operated on a basis of the image pickup signal outputted from the image pickup means. Because of this feature, it is possible to continuously measure the thickness of the coating layer of the container which is sequentially transported in the transporting line of the container, thus enabling the overall measurement of the thickness of the coating layer of all the containers.

In order to attain the above-mentioned purposes, a method for inspecting a coating layer of the sixteenth invention is a method according to the eleventh invention, which comprises:

in the image pickup step, the image pickup means is placed at a location to receive the scattered light produced upon a transmission of the inspecting light through the container;

in the operating step, the standard data comprises data indicating an amount of scattered light premeasured correspondingly to a deteriorating situation, and a deteriorating situation of the coating layer of the container is operated by comparing a data indicated by the image pickup signal with the standard data.

In the method for inspecting a coating layer of the sixteenth invention, when the transmission light is caused to scatter at the time the inspecting light passes through the container, the scattered light is received by the image pickup means. The scattering of the inspecting light is caused to produce by the so-called pinholes formed in the coating layer when the coating layer of the container deteriorates, and the amount of the scattered light increases as the deterioration of the coating layer progresses. The deteriorating situation of the coating layer of the container is operated by comparing the data indicating the amount of the scattered light contained in the image pickup signal with the standard data indicating an amount of the scattered light preset accordingly to a deteriorating situation of a coating layer.

As described above, according to the sixteenth invention, it is possible to automatically differentiate the deteriorating situation of the coating layer formed on the surface of the container and the like on a basis of an objective standard, and to carry out a speedy inspection.

In order to attain the above-mentioned purposes, a method for inspecting a coating layer of the seventeenth invention is a method according to the sixteenth invention, which comprises:

in the inspecting light irradiating step, a slit type inspecting light is irradiated by passing the inspecting light through a slit placed between a light source and a inspecting location of the container.

In the method for inspecting a coating layer of the seventeenth invention, the slit type inspecting light is produced by passing the light irradiated from the light source through the slit formed in the slit member, and is irradiated to the container. As a result, an unnecessary diffusion of the inspecting light is prevented by passing the light irradiated from the light source through the slit and then, irradiating to the container, and the affection of the inspecting light excluding the scattered light produced in accordance with the deterioration of the coating layer is reduced, thus enabling a further precise inspection.

In order to attain the above-mentioned purposes, a method for inspecting a coating layer of the eighteenth invention is a method according to the seventeenth invention, which comprises:

in the inspecting light irradiating step, a plurality of slit are provided.

In the method for inspecting a coating layer of the eighteenth invention, since the slit member has a plurality of slits, a plurality of slit type inspecting lights are irradiated to one container. As a result, it is not necessary to strictly locate the container to be inspected at the inspecting location, thus enabling to carry out an easier and more reliable inspection.

In order to attain the above-mentioned purposes, a method for inspecting a coating layer of the nineteenth invention is a method according to the sixteenth invention, which comprises:

in the image pickup step, the image pickup means is placed at a location to only receive the scattered light and not to receive the inspecting light passing through the container without producing the scattered light.

In the method for inspecting a coating layer of the nineteenth invention, the image pickup means receive only the scattered light produced by the deteriorated coating layer out of the inspecting light passing through the container and does not receive the transmission light passing through without producing the scattering. As a result, it is possible to carry out a correct inspection without being affected by the light which does not indicate the deteriorating situation of the coating layer, and to easily identify a minimal difference of the deterioration of the coating layer.

In order to attain the above-mentioned purposes, a method for inspecting a coating layer of the twentieth invention is a method according to the seventeenth invention, which comprises:

in the operating step, a placement of a transported container to be placed at a prescribed inspecting location is detected, and the deteriorating situation is operated on the basis of the image pickup signal outputted from the image pickup means upon detecting for the container to be placed at the prescribed inspecting location.

In the method for inspecting a coating layer of the twentieth invention, when the inspection of the coating layer is sequentially carried out to the containers transported by the transporting means like a conveyer or the like, it is detected that the transported container is placed at the specific inspecting location. Then, the deteriorating situation of the coating layer is operated on a basis of the image pickup signal outputted from the image pickup means when the container is detected to be placed at the specific inspecting location. Thus, it is possible to automatically and sequentially inspect the coating layers of the containers which are continuously transported in the container transporting line.

BRIEF DESCRIPTION OF THE DRAWINGS

FIG. 6 is a descriptive view illustrating a placement of the apparatus for inspecting a coating layer in the third embodiment of the present invention with a single slit provided.

FIG. 7 is a descriptive view illustrating a placement of the apparatus for inspecting a coating layer in the third embodiment of the present invention with two slits provided.

FIG. 8 is a descriptive view illustrating situations of a pickup image of a scattered light.

BEST MODE FOR CARRYING OUT THE INVENTION

Hereinbelow, preferred embodiments of the present invention are described with reference to the drawings.

Figure 1:
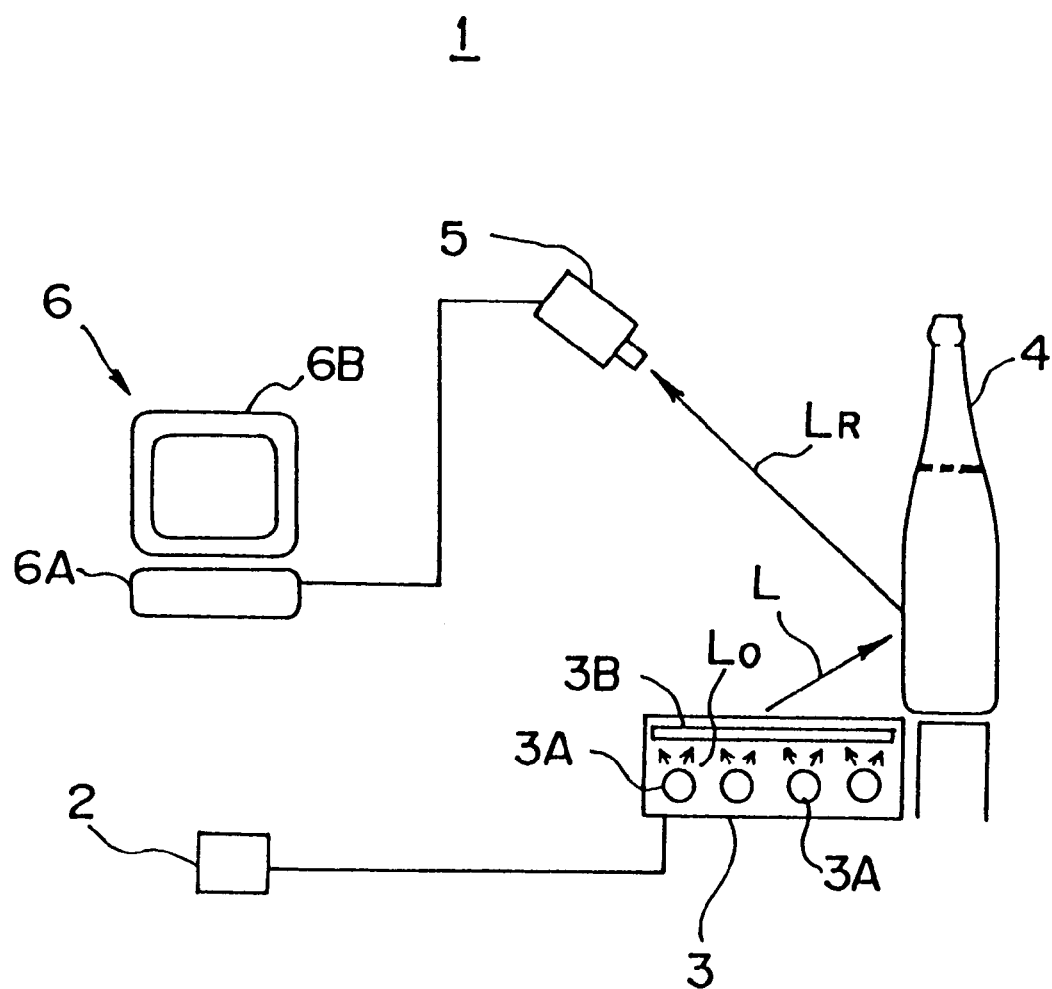
FIG. 1 is a schematic structural view illustrating an apparatus for inspecting a coating layer in the first embodiment of the present invention.

FIG. 1 illustrates an apparatus for inspecting a coating layer of the first embodiment of the present invention. The inspecting apparatus of FIG. 1 measures a thickness of the coating layer formed on a bottle off the production line.

In FIG. 1, an apparatus 1 for inspecting a coating layer includes a light source unit 3 for emitting an inspecting light L to a bottle 4, a stabilized power source 2 connected to the light source unit 3 for supplying a stable power source to the light source unit 3 such that an amount of a light emission of the inspecting light L and an emission spectral distribution becomes constant, a color CCD camera 5 for receiving a reflected light LR of the inspecting light L reflected from the bottle 4, and converting the reflected light LR to a RGB image pickup signal V and outputting same, and an operating unit 6 connected to the color CCD camera 5 for operating a thickness of a coating layer formed on the surface of the bottle on the basis of the inputted RGB image pickup signal V.

The light source unit 3 includes a plurality of white light sources 3A for irradiating an original inspecting light LO, and a diffusion plate 3B for diffusing the original inspecting light LO irradiated from the white light source 3A to produce a uniform surface illuminant. As the white light source 3A, a white fluorescent lamp is applied, because the spectral distribution of the white fluorescent lamp is flat, the color temperature variation thereof is almost constant, and the color temperature correction thereof is not necessary.

In addition, the light source unit 3 is provided to emit the inspecting light L in such manner that the angle of the light axis to the measuring plane of the coating layer of the bottle falls within a range of 30° to 60°. The reason of the angle set as above is that an affection of the thickness variation of the coating layer exerted to the spectral distribution of the reflected light LR can be surely measured.

The operating unit 6 includes an operating unit body 6A for performing actual calculation and various controls, and a display unit 6B for displaying various operating results and controlling situations.

Now, the function of the above-mentioned apparatus 1 for inspecting a coating layer is described in detail.

The stable power source is supplied from the stabilized power source 2 to the white light source 3A of the light source unit 3. Then, the white light source 3A irradiates the original inspecting light LO having a prescribed emission spectral distribution toward the diffusion plate 3B. The diffusion plate 3B diffuses the original inspecting light LO irradiated from the white light source 3A to produce the uniform surface illuminant, from which surface illuminant the inspecting light is irradiated toward the bottle 4.

In the coating layer of the bottle 4 to which the inspecting light is irradiated, the irradiated inspecting light L is absorbed, reflected or interfered, depending on the thickness of the coating layer, and then, the reflected light LR, which has a different spectral distribution from that of the incident inspecting light L, is produced.

In this case, if the coating layer is not formed on the surface of the bottle 4, excluding the influence of the bottle itself, the reflected light LR has the same spectral distribution as those of the inspecting light L. However, as the coating layer is formed thereon, the reflected light LR becomes bluish, as the thickness becomes thicker, and when the thickness reaches 40 nm, the reflected light LR becomes the most bluish. When the thickness becomes thicker than 40 nm, the reflected light becomes golden.

The reflected light LR from the bottle 4, in which a color tone variation (i.e., spectral distribution variation) is produced as describe above, is received by the color CCD camera 5 and converted therein to the RGB image pickup signal V, and outputted to the operating unit 6.

The operating unit 6 operates in the operating unit body 6A the thickness of the coating layer formed on the surface of the bottle 4 on the basis of the RGB image pickup signal inputted from the color CCD camera 5, and then displays the operated thickness of the coating layer on the displaying unit 6B.

The operating process of the thickness of the coating layer in the operating unit body 6A is as follows:

Although there are various means to express the spectral distribution, the XYZ calorimetric system prescribed in JIS (Japanese Industrial Standards) Z 8701 is used hereinbelow.

Figure 2:
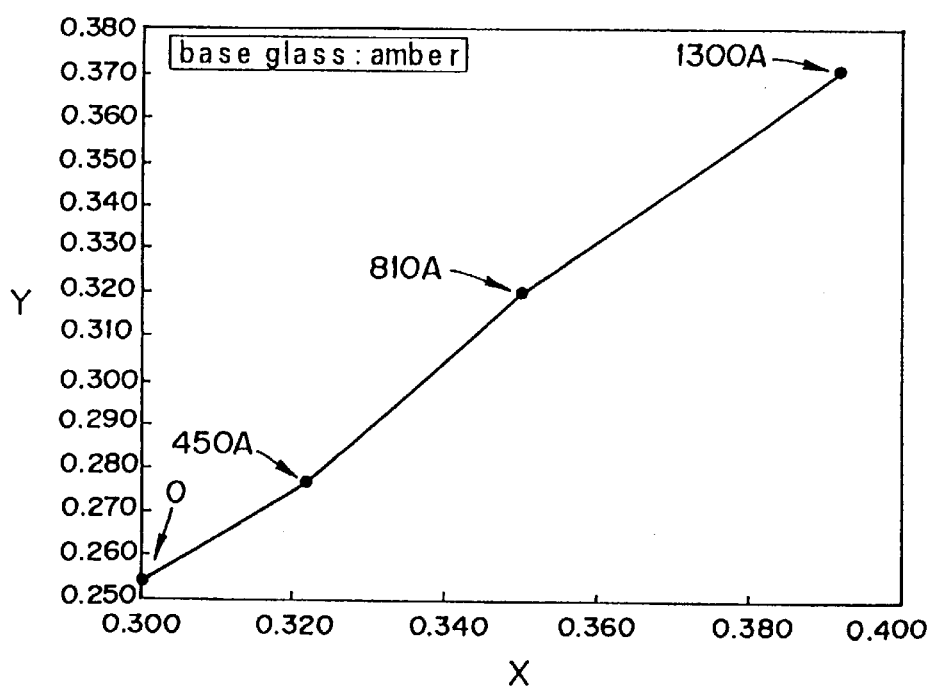
FIG. 2 is a table and graph describing a process of establishing a standard data in the apparatus for inspecting a coating layer in the first embodiment of the present invention.

In FIG. 2, there is illustrated the relationship between the thickness of the coating layer and the bistimulus values X and Y of the light source color in the XYZ calorimetric system in case that the color of the bottle 4 to be measured is amber.

FIG. 2(a) shows the bistimulus values X and Y for each thickness, wherein the coating layers having different thicknesses are premeasured by means of other process, for example, the process of imaging the cross-section of the coating layer by means of an electron microscope, and then, the inspecting light L is irradiated to the coating layer whose thickness is already measured to obtain the bistimulus values X and Y from the reflected light LR thereof.

FIG. 2(b) is a graph illustrating the relationship between the measured thickness of the coating layer and the bistimulus values X and Y, as thus obtained, wherein the stimulus value X is taken along the horizontal axis and the stimulus value Y is taken along the vertical axis. As is clear from FIG. 2(b), the graph indicating the relationship between the coating thickness of the coating layer and the bistimulus values X and Y can be almost approximated by a linear line.

The operating unit body 6A operates the thickness of the coating layer based on the approximate formula obtained from FIG. 2(b). More specifically, the operating unit body 6A obtains the bistimulus values X and Y in the reflected light LR from the RGB image pickup signal V inputted from the color CCD camera 5, based on the reference formula shown in JIS Z 8701, and then operates the thickness of the coating layer from the approximate formula obtained from FIG. 2(b) with the use of thus obtained bistimulus values X and Y.

Then, the thickness of the coating layer thus operated is displayed on the displaying device 6B by the control of the operating unit body 6A.

Figure 3:
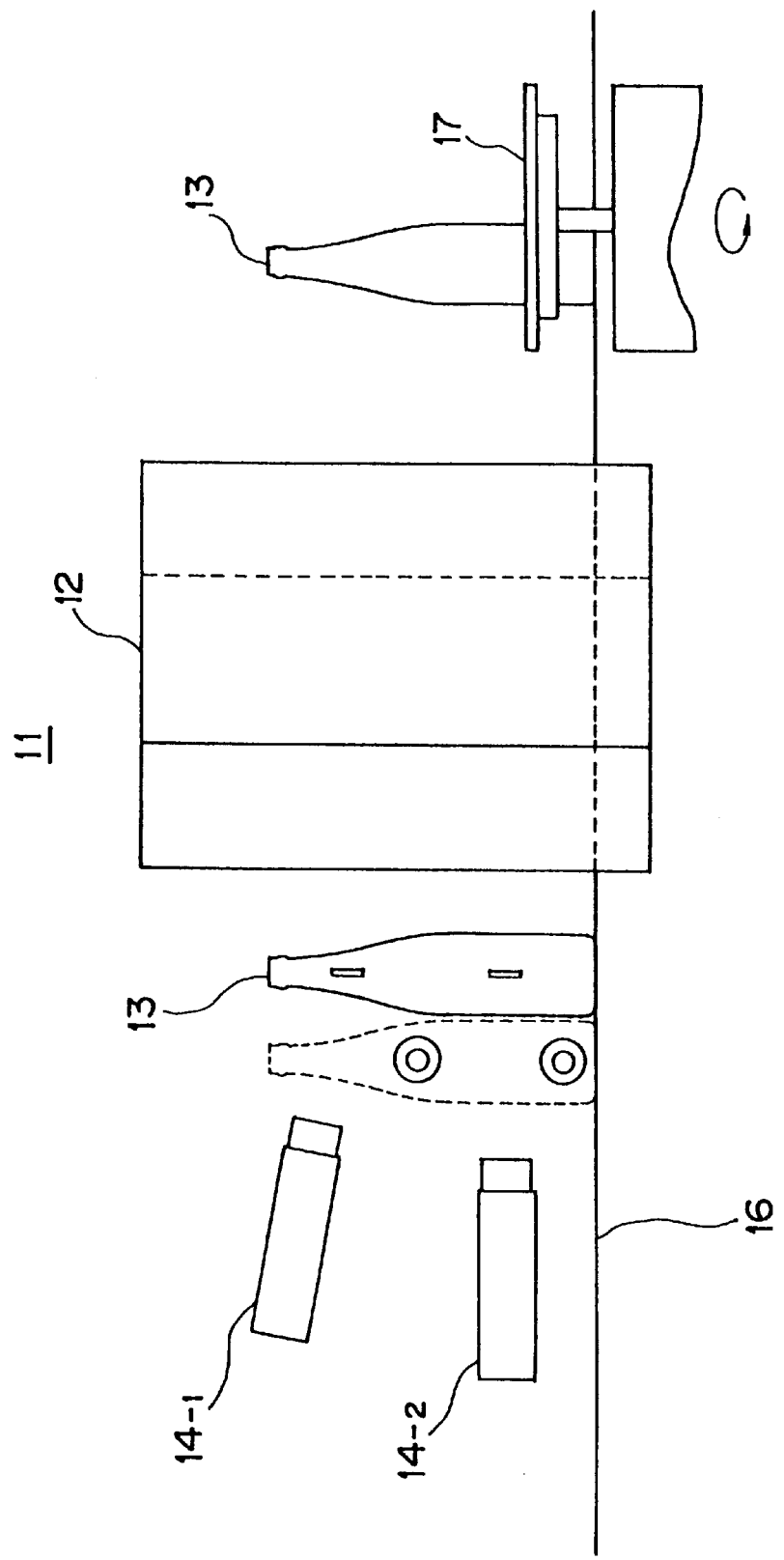
FIG. 3 is a schematic frontal view illustrating an apparatus of inspecting a coating layer in the second embodiment of the present invention.
Figure 4:
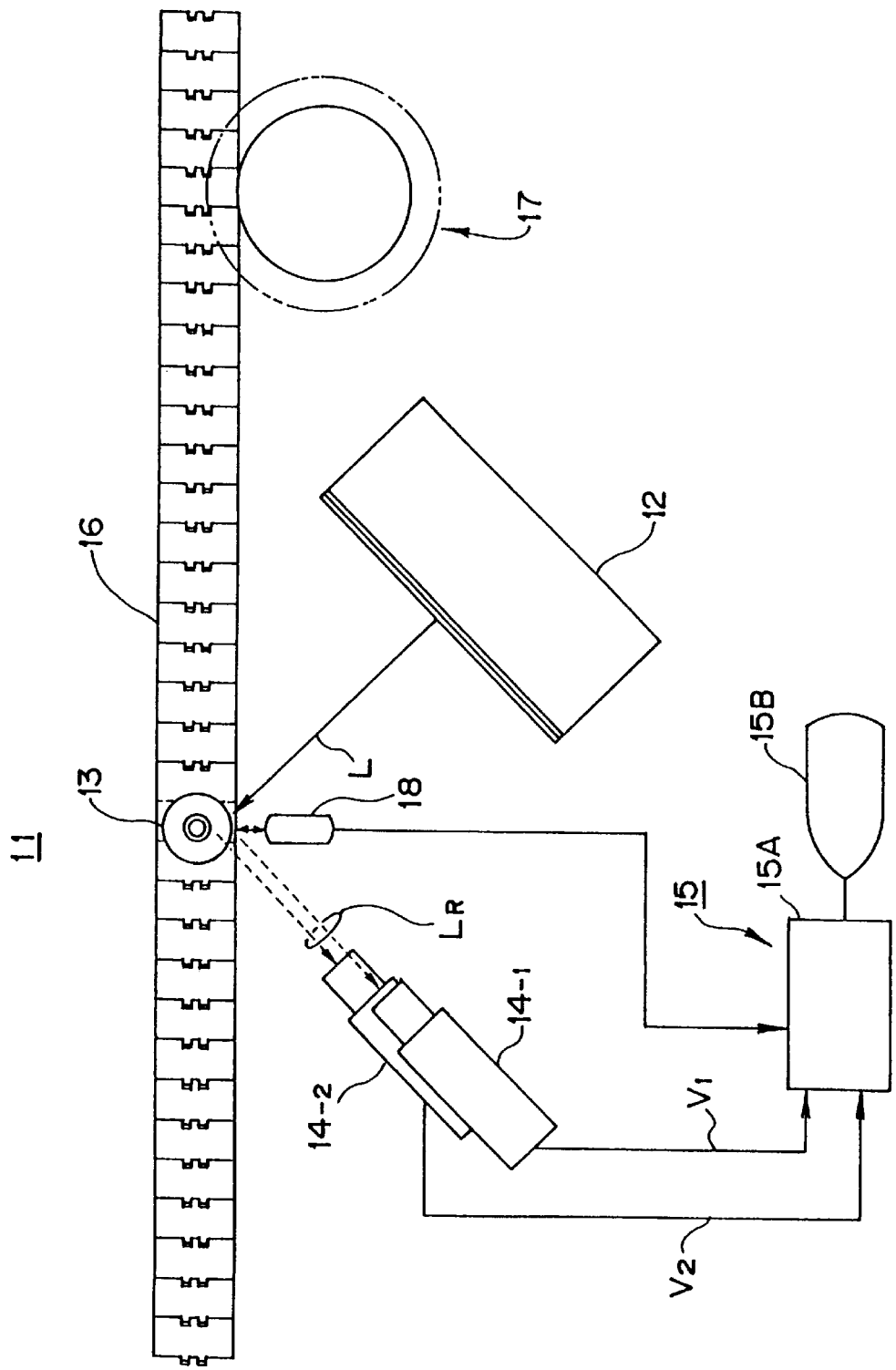
FIG. 4 is a schematic plan view illustrating the apparatus for inspecting a coating layer in the second embodiment of the present invention.

FIGS. 3 and 4 illustrate the second embodiment of the apparatus for inspecting the coating layer of the present invention. FIG. 3 is a schematic frontal view of the inspecting apparatus 11 in the second embodiment. FIG. 4 is the schematic plan view of the inspecting apparatus 11.

The inspecting apparatus 11 measures the thickness of the coating layer of the bottle on the production line, while the inspecting apparatus 1 in the first embodiment measures same off the production line.

In FIGS. 3 and 4, the inspecting apparatus 11 includes a light source unit 12 for irradiating the inspecting light L to the bottle 13 on a transporting conveyer 16, a color CCD camera 14-1 for receiving the reflected light LR of the inspecting light L reflected from the bottle 13, converting the reflected light LR to the RGB image pickup signal V1 and outputting same, a color CCD camera 14-2 for receiving the reflected light LR, converting the reflected light LR to the RGB image pickup signal V2 and outputting same, a control unit 15 for being inputted the RGB image pickup signal V1 and V2 from the color CCD camera 14-1 and 14-2, operating the thickness of the coating layer of the bottle 13 based on the inputted RGB image pickup signal V1 and V2, and controlling the overall apparatus, an infeeder 17 for supplying the bottle 13 onto the transporting conveyer 16 at the prescribed interval, and a location sensor 18 for detecting that the bottle 13 arrives at a measuring location.

The inspecting apparatus 11 includes two color CCD cameras 14-1 and 14-2 because it is possible to measure the coating layer at the plural portions of the bottle 13 such as a neck portion and a central portion of the bottle 13 with the use of two cameras.

The control unit 15 includes the control unit body 15A for operating a thickness of the coating layer and performing various controls, and the displaying device 15B for displaying the operating result and controlling situation and the like.

The working process of the above inspecting apparatus 11 is as follows:

The bottle 13 to be measured is supplied onto the transporting conveyer 16 by the infeeder 17 at the prescribed interval, and is transported to the measuring location by the transporting conveyer 16. Then, when it is detected by the location sensor 18 that the bottle 13 arrives at the measuring location, the detecting signal is outputted from the location sensor 18 to the control unit body 15.

The control unit body 15 starts operating the thickness of the coating layer by the inputted detecting signal from the location sensor 18.

A stable power source is supplied from the stabilized power source (not shown) to the light source unit 12, and the inspecting light L having a prescribed emission spectral distribution is irradiated toward the bottle 13 from the light source unit 12.

In the coating layer formed on the surface of the bottle 13, the phenomenon such as the absorption, reflection, interference or the like of the inspecting light corresponding to the thickness of the coating layer occurs and then, the reflected light LR, which has a different spectral distribution from that of the inspecting light L, is produced.

The reflected light LR reflected from the bottle 13 is received by the two color CCD cameras 14-1 and 14-2, and converted to the RGB image pickup signal V1 and V2 and outputted to the control unit 15, respectively.

The control unit 15, by means of the same process described in the first embodiment with reference to FIGS. 2(a) and (b), operates the thickness of the coating layer of the bottle 13 through the RGB image pickup signal V1 and V2, respectively. Then, the respective thickness of the coating layers operated in each color CCD cameras is displayed on the displaying device 15.

As described above, according to the above inspecting apparatus 11, it is possible to measure the thickness of the coating layer of all the bottles sequentially and without contacting the bottle in the manufacturing process. Thus, it is possible to improve the reliability of the coating layer applied on the surface of the bottle, and in addition, it is possible to carry out the speedy measurement of the coating layer because the thickness of the coating layer is measured automatically without handling by hand.

In the above respective embodiment, the XYZ calorimetric system is applied to compare the spectral distribution, however, it is possible to apply the other means as far as the spectral distribution can be differentiated in quantity.

Figure 5:
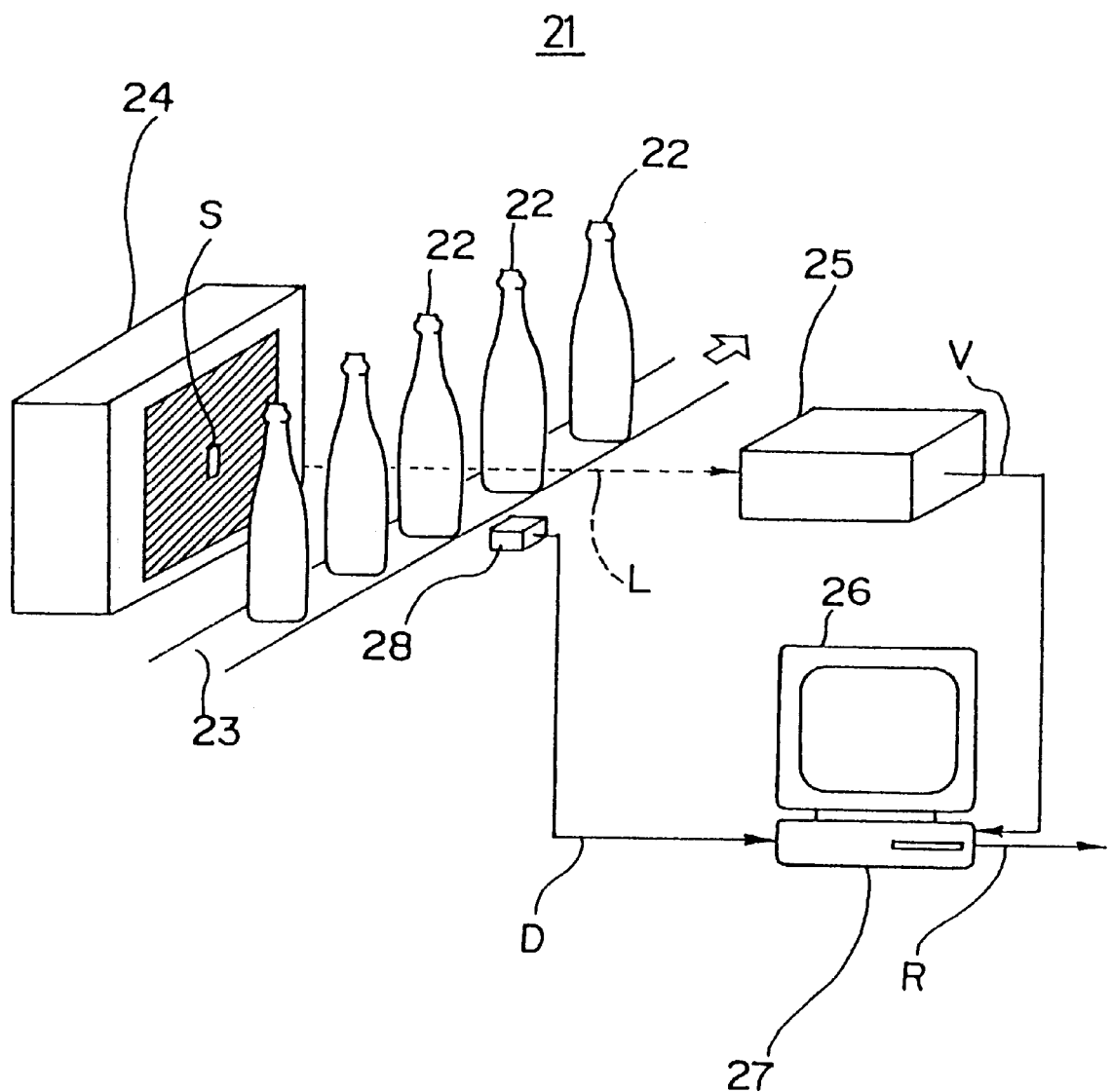
FIG. 5 is a schematic structural view illustrating an apparatus for inspecting a coating layer in the third embodiment of the present invention.

FIG. 5 illustrates the third embodiment of the apparatus for inspecting a thickness of the coating layer of the present invention. The inspecting apparatus of FIG. 5 inspects the deteriorating situation of the coating layer formed on the bottle.

In FIG. 5, the inspecting apparatus 21 includes a inspecting light emitting unit 24, provided facing to the side portion of a conveyer 23 transporting a bottle 22 to be inspected and having therein a light source (not shown) of such as a fluorescent lamp of about 30 Watt, for emitting the inspecting light L from a slit S provided on the side of the conveyer 23, a image pickup unit 25 comprising a CCD camera provided at the location of the opposite side of the inspecting light emitting unit 24 with the conveyer 23 therebetween as well as at the location of receiving only a scattering light scattered from the coating layer of the bottle 22 out of the whole inspecting light L emitted from the inspecting light emitting unit 24, a control unit 27 for operating a deteriorating situation of the coating layer formed on the bottle 22 based on an image pickup signal V inputted therein from the image pickup unit 25, a displaying device 26 for displaying a result operated in the control unit 27 as well as the pickup image obtained through the image pickup signal V from the image pickup unit 25, and a location sensor 28 for detecting that the bottle 22 arrives at an inspecting location and outputting a location detecting signal D.

The side wall of the inspecting light emitting unit 24 with the slit S is formed thereon, facing toward the conveyer 23, is painted black. This enables to more distinctly detect the scattering situation of the scattered light when the bottle 22 is imaged by the image pickup unit 25.

Now, the relative locations of the emitting direction of the inspecting light L and the image pickup unit 25 are described with reference to FIGS. 6 and 7.

FIG. 6 shows an example of the relative location thereof in case that a single slit S is provided.

In FIG. 6, the inspecting light L irradiated from the light source through the slit S to the bottle 22 to be inspected passes through the bottle 22. The optical pass of the inspecting light after passing through the bottle 22 becomes the straight line in accordance with the optical pass of the original inspecting light L before being incident on the bottle 22 in case that a scattered light is not produced at the time the inspecting light L passes through the bottle 22, as shown in the solid line. On the other hand, the optical pass of the inspecting light L after passing through the bottle 22 becomes refracted in relation to the optical pass of the original inspecting light L before being incident on the bottle 22 in case that a scattered light is produced at the time the inspecting light L passes through the bottle 22, as shown in the dotted lines.

The image pickup unit 25 is provided in the optical pass of the scattered light (i.e., the optical pass shown in dotted line). This enables that the scattered light of the inspecting light L is incident on the image pickup unit 25 only in case that the scattered light is produced at the time the inspecting light L passes through the bottle 22, on the other hand, the emission light of the inspecting light L is not incident on the image pickup unit 25 in case that the scattered light is not produced at the time the inspecting light L passes through the bottle 22.

FIG. 7 shows an example of the relative location thereof in case that a plurality of slits S (in this example, two slits) are provided.

In this example, as shown in FIG. 7(b), two slits S are respectively formed at the location where two straight lines L1, L2', each of which intersects by the prescribed angle θ a straight line L1 containing an optical axis of the image pickup unit 25 and passing through the center of the bottle 22, intersect the front wall of inspecting light emitting unit 24.

In the above example, the straight line L1 between the bottle 22 and the image pickup unit 25 indicates an optical pass of the scattered light when the scattered light is produced at the time the inspecting light L is irradiated from the slit S to the bottle 22. In addition, two straight lines L2, L2' indicate optical passes when the inspecting light L is not scattered at the time the inspecting lights L pass through the bottle 22.

The angle θ is set up in such manner that the image pickup unit 25 is not located on both of the respective two straight lines L2, L2'.

According to the above mentioned relative location of the image pickup unit 25 and each slit S, as shown in FIG. 7(a), the optical pass of the scattered light is refracted from the original optical pass and becomes in accordance with the optical axis of the image pickup unit 25, as shown in dotted line, in case that the scattering is produced at the time the inspecting lights L emitted from each of the slits S pass through the bottle 22 to be inspected, thus the scattered light of the inspecting light L is incident on the image pickup unit 25.

On the other hand, when the inspecting lights L emitted from each of the slits S are not scattered at the time the inspecting lights L pass through the bottle 22 to be inspected, the optical pass of the emission lights becomes straight lines in accordance with the original optical pass of the inspecting light L, as shown in the solid lines, thus the emission light of the inspecting light L is not incident on the image pickup unit 25.

The reason why a plurality of slits S are provided in the above example is that by use of the inspecting lights L irradiated to the bottle 22 from a plurality of slits S, it is possible to expand the range of the location of the bottle for inspection wherein the inspection can be carried out for the bottle. Thus, by use of a plurality of slits S, the accuracy of the location of the bottle for the inspection is not required so strictly, resulting in the simplification of the construction of the inspecting apparatus.

Figure 13:
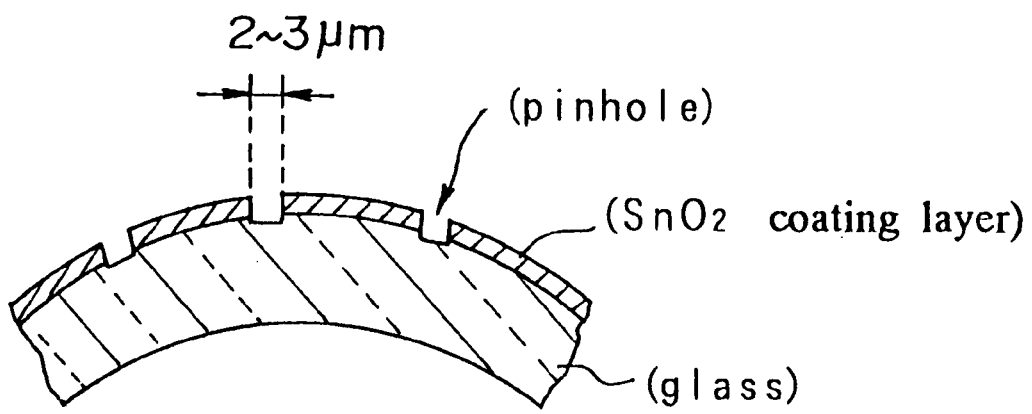
FIG. 13 is a descriptive view illustrating a deteriorating situation of a coating layer.
Figure 13:
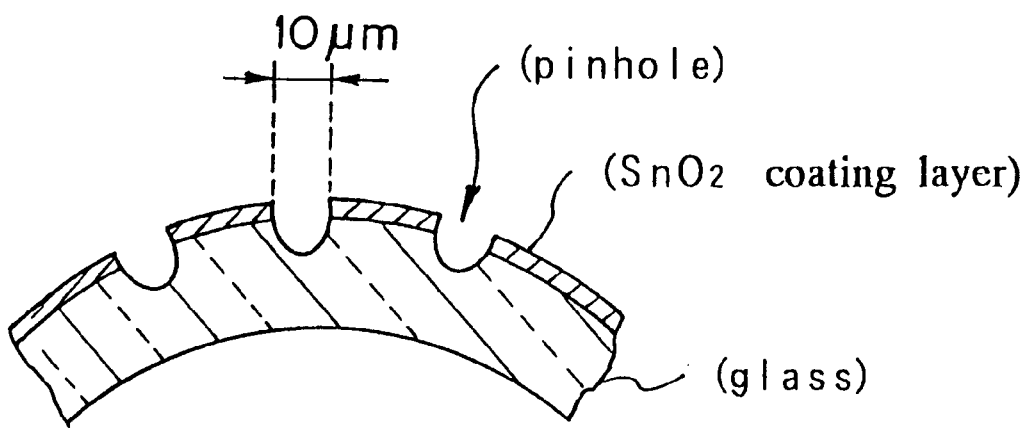

The inspecting principle of the above-mentioned inspecting apparatus 21 is as follows:

As described in relation to FIG. 13, when the coating layer formed on the surface of the bottle is deteriorated because of a repetitive washing of the bottle to form the pinhole in the coating layer, the light is scattered by the pinhole at the time the light passes through the bottle. The amount of the scattered light becomes larger as the diameter of the pinhole formed in the coating layer becomes larger.

In the inspecting apparatus 21, the relationship between the diameter of the pinhole in the coating layer (which corresponds to a deteriorating situation of the coating layer) and the amount of the scattered light passing through the bottle is memorized in advance in the control unit 27, the inspection of the deteriorating situation of the coating layer is carried out by comparing the detected amount of the scattered light in the bottle 22 to be inspected with the memorized relationship.

The function of the inspecting apparatus 21 on the basis of the above inspecting principle is described hereinbelow.

The inspecting light emitting unit 24 irradiates the inspecting light L from the slit S provided on the side facing the conveyer 23 toward the image pickup unit 25. When the bottle 22 to be inspected is transported by the conveyer 23, the inspecting light L mentioned above is irradiated to the bottle 22.

Then, when it is detected by the location sensor 28 that the bottle 22 arrives at the inspecting location (i.e., the location where the inspecting light L passes the center of the bottle 22), the location detecting signal D is outputted from the location sensor 28 to the control unit 27. Then the control unit 27 starts operating the deteriorating situation of the coating layer through the location detecting signal D inputted therein.

The inspecting light L incident on the bottle 22 produce a scattered light correspondingly to the deteriorating situation of the coating layer (i.e., the situation of the pinhole formed therein), and then, the scattered light is incident on the image pickup unit 25.

FIG. 8 illustrates images of the scattered light taken by the image pickup unit 25.

In FIG. 8, (A-1) to (A-3) show diagrammatic images of the bottle 22 with the surface thereof dried, and (B-1) to (B-3) show diagrammatic images of the bottle 22 with the surface thereof wetted.

The images (A-1) and (B-1) are those in which the coating layer is not deteriorated or the deterioration is smaller. As is shown, there is observed almost no scattered light near the central portion of the images which is indicated by the cross in the drawings.

Figure 9:
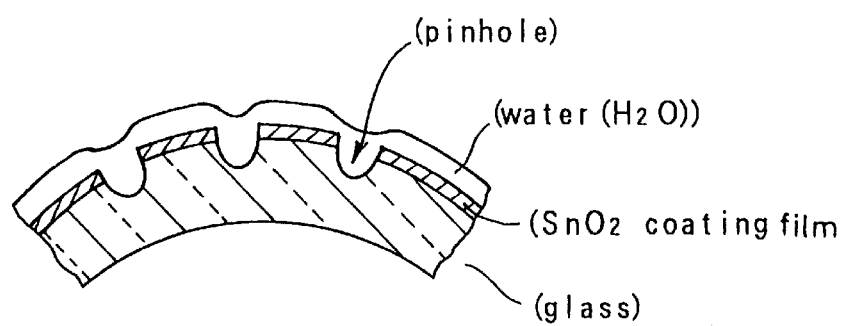
FIG. 9 is a partial cross-sectional view illustrating a situation of a bottle with a coating layer deteriorated in a wetted situation.

The images (A-2) and (B-2) are those in which the deterioration of the coating layer is in the medium degree. As is shown, there is observed the scattered light near the central portion of the image in FIG. 8 (A-2), while there is not observed the scattered light near the central portion of the image in FIG. 8 (B-2) in which the bottle is in a wetted situation. This is because the pinhole formed in the coating layer is masked by the water to function as if the diameter of the pinhole becomes smaller, as shown in FIG. 9, thus reducing the scattered light.

The images (A-3) and (B-3) are those in which the deterioration of the coating layer progress to the extent that the diameter of the pinhole becomes so large that the bottle has to be discarded. As is shown, there is observed the scattered light near the central portion of the respective images in both situations in which the respective surfaces of the bottles is in either the dried or wetted situation.

As described above, as the degree of the deterioration of the coating layer becomes higher, the portion in which the scattered light is detected becomes wider in the image.

The control unit 27 operates the inspecting data, when the location detecting signal D is inputted from the location sensor 28 by taking therein the image pickup signal V inputted from the image pickup unit 25, making the image pickup signal V binary coded, and then, carrying out the various operations such as distribution analysis of the scattered light on the basis of the image pickup signal V which is made binary coded.

Then, the control unit 27 operates the deteriorating situation of the coating layer in the bottle 22 to be inspected by comparing the obtained inspecting data with the standard data memorized in advance (which is described later in detail).

The operating results of the coating layer and the pickup image of the scattered light at that time are displayed on the displaying device 26. When the deterioration of the coating layer progress to the extent as shown in FIG. 8 (A-3) and (B-3) as the operating results, the control unit 27 outputs a rejecting signal to a rejecting apparatus (not shown) provided at the downstream side of the conveyer 23 to exclude the bottle 22.

As described above, according to the inspecting apparatus 21, the inspection of the coating layer can be automatically and continuously carried out without producing unreliable inspecting results by means of easily and objectively grasping the external appearance, which is produced as a result of the deterioration of the coating layer in a micron order on the basis of the amount or distribution of the scattered light at the time the light passes through the bottle.

The standard data which is memorized in advance in the control unit 27, mentioned above, can be obtained by the following process.

Firstly, the deteriorating degree of the coating layer of the bottle to be inspected are classified to the six grades (from grade 0 to grade 5) by observation with eyes. More specifically, the situation in which the coating layer is not deteriorated is defined as grade 0, the situation in which the coating layer is deteriorated to the extent for the bottle to be discarded is defined as grade 5, and then, the situations therebetween are classified to five grades.

Then, in order to convert the deteriorating situation of the bottle into a numeral value, the numeral value of the deteriorating situation of the bottle in the grade 0 is established as 50, and the numeral value of the deteriorating situation of the bottle in the grade 5 is established as 100.

Figure 10:
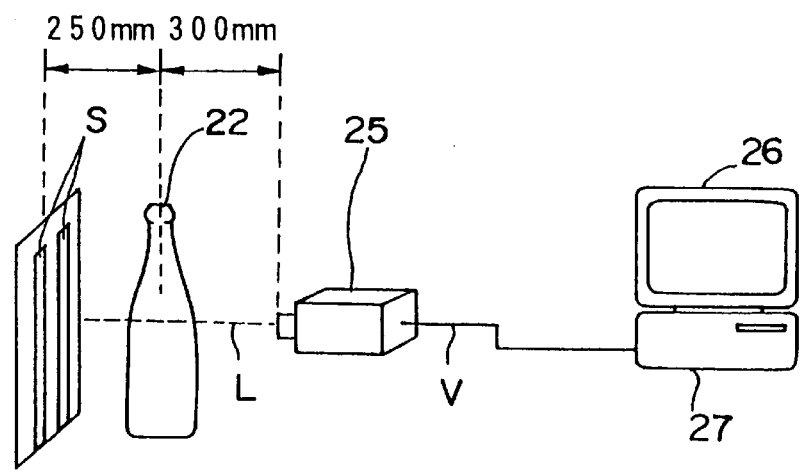
FIG. 10 is a schematic structural view illustrating a measuring device for establishing a standard data in the third embodiment of the present invention.

The bottles classified to each grades by the observation with eyes are prepared so as to have plural bottles in each grades, each of the bottles is imaged by the measuring device shown in FIG. 10, and the numeral value indicating the deteriorating situation of the respective bottles is operated by comparing the pickup image with the image of the bottle the deteriorating situation of which is thus converted into the numeral values.

Figures 11, 12:
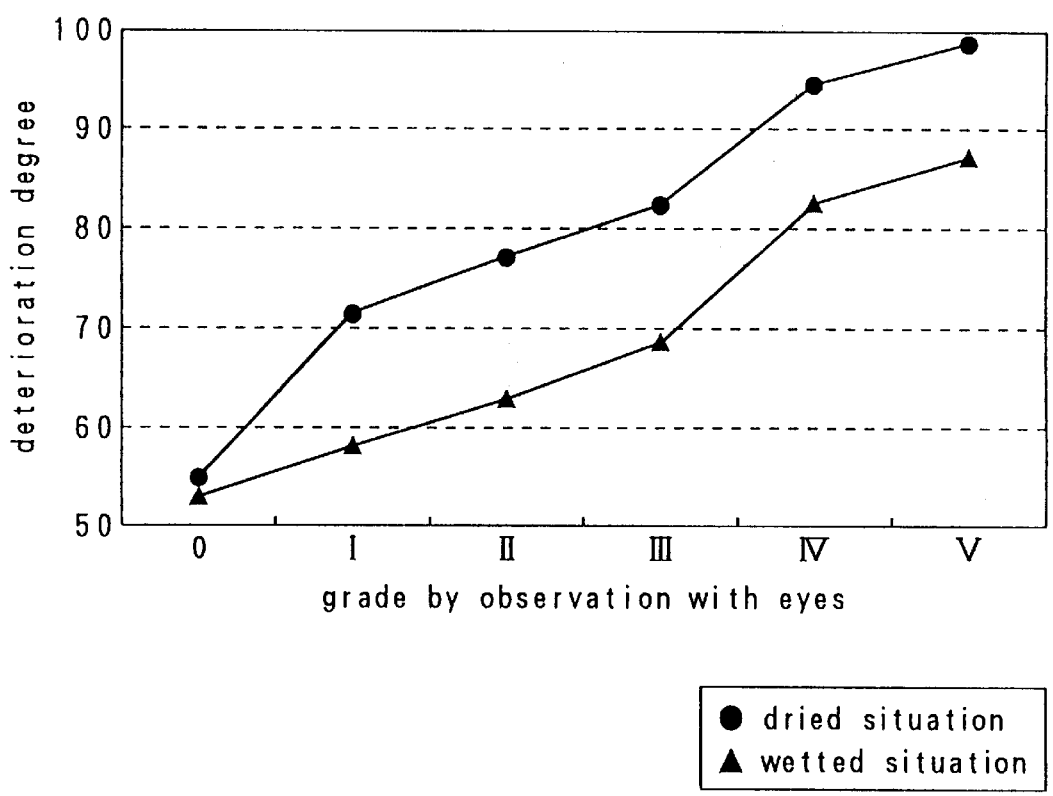
FIG. 11 is a table describing a process of establishing a standard data in the third embodiment of the present invention.
FIG. 12 is a graph corresponding to the table in FIG. 11.

FIG. 11 is the table showing the mean value of the results inspected in each grades. FIG. 12 is the graph based on the table in FIG. 11.

Thus obtained numeral values indicating the deteriorating situation of the bottle is memorized in the control unit 27 as the standard data. The control unit 27 operates the deteriorating situation of the coating layer by comparing the image pickup data obtained by imaging the bottle to be inspected with the standard data to differentiate the bottles to be inspected to each grades. Then, the bottle 22 over the grade defined in advance are identified as a bad quality.

In FIGS. 11 and 12, there are shown the respective measured results in both situations of the bottle with the surface thereof dried as well as the bottle with the surface thereof wetted.

When the measured result in the situation of the bottle with the surface thereof dried is compared with those in the situation of the bottle with the surface thereof wetted, it is realized that there is almost no difference between two measured results in relation to the grade 0, however, the measured results in the situation of the bottle with the surface thereof dried are larger by 11 to 14 than those in the situation of the bottle with the surface thereof wetted in relation to the grades 1 to 5.

Accordingly, for example, when the standard data for the bottle with the surface thereof dried is memorized in the control unit 27, and the numeral values of the difference in the measured results in the above situations of the bottles with the surface thereof dried and wetted is memorized as an amendment value, it is possible to carry out a high accuracy inspection even to the bottle in the wetted situation for example immediately after washing.

The measuring conditions in the measuring device in FIG. 10 are as follows:

A fluorescent lamp is used as a light source, two slits S are provided with the interval between two slits being 50 mm, the slit width being 8 mm, the distance from the slit S to the bottle 22 being 250 mm, and the distance from the bottle to the color CCD camera 25 as the image pickup unit being 300 mm. The bottle to be inspected is a brown beer bottle.

The inspection according to the inspecting apparatus 21 can be carried out not only to the brown bottle but also to a white or green bottle, only when the standard data is changed to the corresponding standard data to the color of the bottle to be inspected.

INDUSTRIAL APPLICABILITY

As described above, the apparatus of the present invention for inspecting a coating layer is applied to inspect a thickness or a deteriorating situation of a coating layer formed on a surface of a bottle like a beer bottle for the purpose of lightening in weight. It is effective in use to prevent a bottle not holding a prescribed strength or a bottle with a largely damaged external appearance due to a deterioration of the coating layer from shipping to a market.

What is claimed is:

1. An apparatus for inspecting a thickness or deteriorating situation of a coating layer formed on a surface of a container, comprising:

an inspecting light irradiating means to irradiate an inspecting light to a container with a coating layer formed thereon;

an image pickup means to receive a reflected light or a transmission light of the inspecting light irradiated by said inspecting light irradiating means and reflected from the container or passing through the container, and to convert the reflected light or the transmission light into an image pickup signal; and a determining means to determine a thickness or a deteriorating situation of the coating layer formed on the container, said thickness and said deteriorating situation being determined by inputting the image pickup signal outputted from said image pickup means and comparing an image pickup data indicated by the image pickup signal with a prememorized standard data.

2. An apparatus for inspecting a coating layer according to claim 1, wherein:

said inspecting light irradiating means irradiates the inspecting light having a prescribed spectral distribution;

said image pickup means is placed at a location to receive a reflected light of the inspecting light from the container;

said standard data comprises a standard spectral distribution premeasured correspondingly to a thickness of the coating layer; and said determining means determines a thickness of the coating layer by comparing a spectral distribution received by said image pickup means with the standard spectral distribution.

3. An apparatus for inspecting a coating layer according to claim 2, wherein:

an irradiating angle of the inspecting light of the inspecting light irradiating means to the coating layer of the container is within a range of 30° to 60°.

4. An apparatus for inspecting a coating layer according to claim 2, wherein:

said inspecting light irradiating means comprises a surface illuminant and a color temperature of the irradiated inspecting light is fixed to be about constant.

5. An apparatus for inspecting a coating layer according to claim 2, wherein:

said apparatus further includes a location detecting means to detect for a transported container to be placed at a prescribed inspecting location, and to output a detecting signal; and said determining means determines a thickness of the coating layer by taking therein the image pickup signal outputted from said image pickup means upon inputting therein the detecting signal outputted from said location detecting means.

6. An apparatus for inspecting a coating layer according to claim 1, wherein:

said image pickup means is placed at a location to receive a scattered light produced upon a transmission of the inspecting light irradiated from the inspecting light irradiating means through the container;

said standard data comprises a data indicating a deteriorating situation of a coating layer prefixed correspondingly to a deteriorating situation of a coating layer; and said determining means determines a deteriorating situation of the coating layer of the container by comparing a data based on an amount of the scattered light received by said image pickup means with said standard data.

7. An apparatus for inspecting a coating layer according to claim 6, wherein:

said image pickup means is placed at a location to only receive a scattered light and not to receive the inspecting light passing through the container without producing the scattered light.

8. An apparatus for inspecting a coating layer according to claim 6, wherein:

said inspecting light irradiating means has a light source and a slit member having a slit placed between said light source and an inspecting location of the container, and producing a slit type inspecting light by passing a light irradiated from the light source through said slit.

9. An apparatus for inspecting a coating layer according to claim 8, wherein:

said slit member has a plurality of slits.

10. An apparatus for inspecting a coating layer according to claim 6, wherein:

said apparatus further includes a location detecting means to detect for a transported container to be placed at a prescribed inspecting location, and to output a detecting signal;

said operating means operates a deteriorating situation of the coating layer by taking therein the image pickup signal outputted from said image pickup means upon inputting therein the detecting signal outputted from said location detecting means.

11. A method for inspecting a thickness or deteriorating situation of a coating layer formed on a surface of a container, comprising:

an inspecting light irradiating step to irradiate an inspecting light to a container with a coating layer formed on a surface thereof;

an image pickup step to receive by an image pickup means a reflected light from a container of the inspecting light irradiated in said inspecting light irradiating step or a transmission light passing through the container, and to convert into an image pickup signal; and a determining step to determine a thickness or a deteriorating situation of the coating layer formed on the container, said thickness and said deteriorating situation being determined by comparing an image pickup data of the image pickup signal of the reflected light or the transmission light converted in said image pickup step with a preset standard data.

12. A method for inspecting a coating layer according to claim 11, wherein:

in said inspecting light irradiating step, the inspecting light comprises a light having a prescribed spectral distribution;

in said image pickup step, said image pickup means is placed at a location to receive the reflected light from the container of the inspecting light; and in said determining step, said standard data comprises a standard spectral distribution premeasured correspondingly to a thickness of a coating layer and a thickness of a coating layer is determined by comparing a spectral distribution of the reflected light indicated by the image pickup signal with the standard spectral distribution.

13. A method for inspecting a coating layer according to claim 12, wherein:

in said inspecting light irradiating step, an irradiating angle of the inspecting light to the coating layer of the container is within a range of 30° to 60°.

14. A method for inspecting a coating layer according to claim 12, wherein:

in said inspecting light irradiating step, a light source comprises a surface illuminant, and a color temperature of the inspecting light irradiated from said surface illuminant is fixed to be about constant.

15. A method for inspecting a coating layer according to claim 12, wherein:

in said operating step, a placement of a transported container at a prescribed inspecting location is detected and a thickness of a coating layer is determined on the basis of the image pickup signal outputted from said image pickup means upon detecting for the container to be placed at a prescribed location.

16. A method for inspecting a coating layer according to claim 11, wherein:

in said image pickup step, said image pickup means is placed at a location to receive the scattered light produced upon a transmission of the inspecting light through the container;

in said determining step, said standard data comprises a data indicating an amount of scattered light premeasured correspondingly to a deteriorating situation, and a deteriorating situation of the coating layer of the container is determined by comparing a data indicated by the image pickup signal with said standard data.

17. A method for inspecting a coating layer according to claim 16, wherein:

in said inspecting light irradiating step, a slit type inspecting light is irradiated by passing the inspecting light through a slit placed between a light source and a inspecting location of the container.

18. A method for inspecting a coating layer according to claim 17, wherein:

in said inspecting light irradiating step, a plurality of slit are provided.

19. A method for inspecting a coating layer according to claim 16, wherein:

in said image pickup step, said image pickup means is placed at a location to only receive the scattered light and not to receive the inspecting light passing through the container without producing the scattered light.

20. A method for inspecting a coating layer according to claim 17, wherein:

in said determining step, a placement of a transported container to be placed at a prescribed inspecting location is detected, and a deteriorating situation is detected on the basis of the image pickup signal outputted from said image pickup means upon detecting for the container to be placed at the prescribed inspecting location.

* * * * *

UNITED STATES PATENT AND TRADEMARK OFFICE
CERTIFICATE OF CORRECTION

PATENT NO. : 5,991,018 Page 1 of 1
DATED : November 23, 1999
INVENTOR(S) : Junjirou Imaizumi, et al.

It is certified that error appears in the above-identified patent and that said Letters Patent is hereby corrected as shown below:

Title Page: Item [87] should be:

--[87] PCT Pub. No.: WO97/00423
   PCT Pub. Date: Jan. 3, 1997--

Signed and Sealed this

Nineteenth Day of June, 2001

*Attest:*

NICHOLAS P. GODICI
*Attesting Officer*   *Acting Director of the United States Patent and Trademark Office*